United States Patent [19]

Castagnola et al.

[11] Patent Number: 4,514,393
[45] Date of Patent: Apr. 30, 1985

[54] NEW DERIVATIVES OF BILIARY ACIDS, PROCESS FOR THE PRODUCTION THEREOF AND PHARMACEUTICAL COMPOSITIONS CONTAINING THE SAME

[75] Inventors: Virginio Castagnola, Milan; Giuliano E. Frigerio, Bresso-Milan; Roberto Pellicciari, Perugia, all of Italy

[73] Assignee: Lehner AG, Muttenz, Switzerland

[21] Appl. No.: 516,251

[22] Filed: Jul. 22, 1983

[30] Foreign Application Priority Data

Jul. 29, 1982 [IT] Italy .................. 22632 A/82
Jul. 1, 1983 [IT] Italy .................. 21909 A/83

[51] Int. Cl.³ ............................. A01N 45/00
[52] U.S. Cl. .............................. 260/397.1
[58] Field of Search .......... 260/397.1; 424/238; 260/397.1

[56] References Cited

U.S. PATENT DOCUMENTS 4,354,972 10/1982 Kaiser .................. 260/397.1

Primary Examiner—Elbert L. Roberts
Attorney, Agent, or Firm—Birch, Stewart, Kolasch & Birch

[57] ABSTRACT

Derivatives of biliary acids having formula I

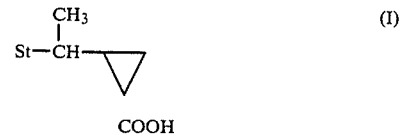

wherein St has the meaning of the 17-etiocholanyl residue, having two or more hydroxyl groups both in the α and β conformation, some of which being optionally replaced by keto groups, and their pharmaceutically acceptable salts with alkaline or alkali-earth metals, or with organic bases.

14 Claims, No Drawings

NEW DERIVATIVES OF BILIARY ACIDS, PROCESS FOR THE PRODUCTION THEREOF AND PHARMACEUTICAL COMPOSITIONS CONTAINING THE SAME

The invention refers to a series of biliary acid derivatives having formula (I):

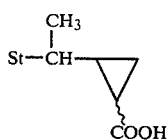
(I)

wherein St has the meaning of the 17-etiocholanyl residue, having two or more hydroxyl groups both in the $\alpha$ and $\beta$ conformation, some of which may be optionally replaced by keto groups, and their pharmaceutically acceptable salts with alkaline or alkali-earth metals, or with organic bases.

The compounds of formula I, and their salts above cited, are endowed with interesting pharmacological properties. The invention refers therefore also to pharmaceutical compositions containing an active ingredient one or more compounds of formula (I) or their pharmaceutically acceptable salts.

Non-limiting examples of compounds I of the present invention are the following ones:

3$\alpha$,7$\alpha$,12$\alpha$-trihydroxy-5$\beta$-cholan-22,23-methanate-24-oic acid (22,23-methanate-cholic acid) (Ia).

3$\alpha$,7$\beta$,12$\alpha$-trihydroxy-5$\beta$-cholan-22,23-methanate-24-oic acid (Ib).

3$\alpha$,7$\beta$-dihydroxy-5$\beta$-cholan-22,23-methanate-24-oic acid (22,23-methanate-ursodeoxycholic acid) (Ic).

3$\alpha$,7$\alpha$-dihydroxy-5$\beta$-cholan-22,23-methanate-24-oic acid (22,23-methanate-chenodeoxycholic acid) (Id).

3$\alpha$-hydroxy-7-keto-5$\beta$-cholan-22,23-methanate-24-oic acid (3$\alpha$-hydroxy-7-keto-22,23-methanate-cholanic acid) (Ie).

The invention refers also to a process for the preparation of the compounds of formula (I), characterized by hydrolyzing corresponding esters having formula (II)

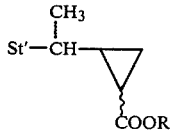
(II)

wherein St' represents the etiocholanyl residue, having two or more acyloxy groups both in $\alpha$ and $\beta$ conformation, or keto groups, and R is a $C_1$-$C_4$ alkyl residue. Preferably, the acyloxy groups are acetoxy groups and R is a methyl or ethyl residue.

The hydrolysis is preferably carried out in basic medium, for instance in an hydroalcoholic solution of an alkali metal hydroxide, such as sodium or potassium hydroxide, at temperatures ranging from 20° to 100° C., preferably at the reflux temperature of the solvent mixtures, for times of between 1 and 12 hours.

Compounds of formula (II) are in turn obtained by a reaction of 24-nor-cholenes (III)

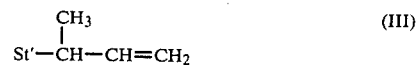

wherein St' has the above mentioned meaning, with alkyl diazoacetates $N_2CH$-COOR (wherein R has the above specified meaning) in the presence of Cu-Bronze and in inert solvents, for instance cyclohexane.

Finally, the 24-norcholenes (III) are prepared by treating the acids (IV)

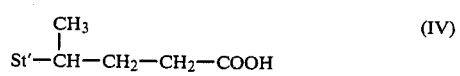

wherein St' has the above specified meanings, with lead tetraacetate (in presence of $Cu^{++}$ ions, preferably of rameic acetate) in pyridine.

The process according to the invention will be more easily understood from the scheme hereinbelow reported for the preparation of 22,23-methanate-ursodeoxycholic acid (Ic):

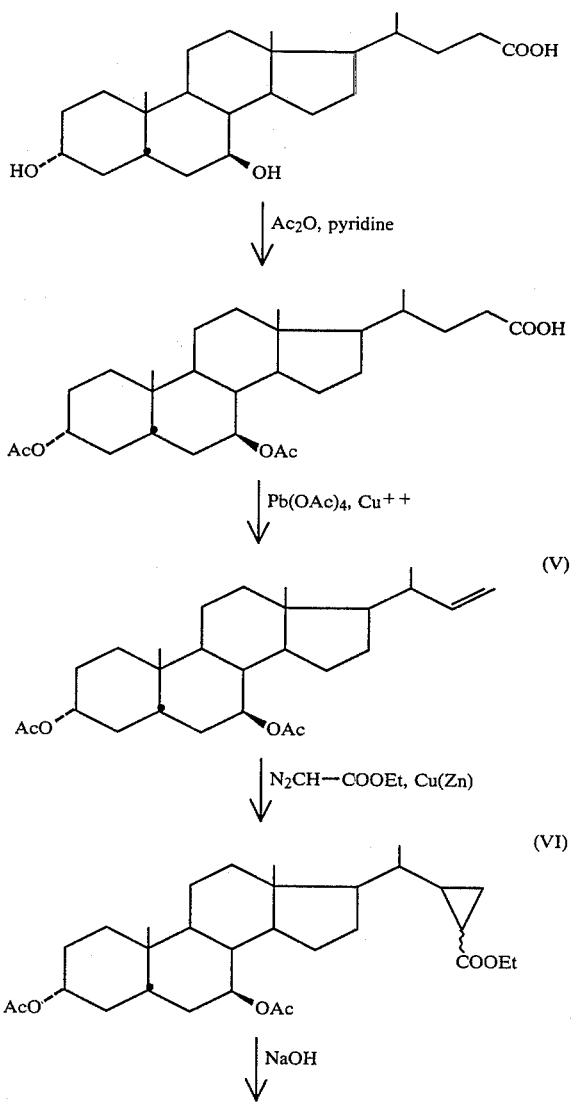

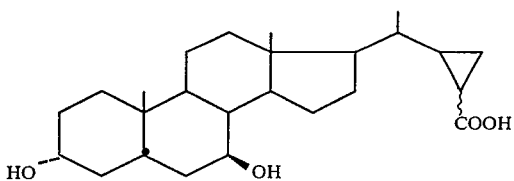

(Ic)

It is plain that the esters (II) of the present invention can be present in two isomeric forms from the steric point of view and that this influences, of course, the acids (I) obtained from the esters themselves. Of course, the invention refers to all possible stereoisomers of the claimed compounds.

The following examples illustrates the process according to the invention, without limiting in any way the scope thereof.

EXAMPLE 1

(a) 3α,7β-Diacetoxy-Δ$^{22}$-24-norcholene (V)

A mixture of ursodeoxycholic acid (I) (40 g), acetic anhydride (60 ml), and pyridine (48 ml) is left to react overnight. The reaction mixture is poured on ice-water and extracted with chloroform. The organic phase is washed with 10% HCl to acidity, then with water to neutrality, dried on MgSO$_4$ and evaporated. The crude product so obtained, without further purification, Pb(OAc)$_4$ (70 g), Cu(OAc)$_2$ (4 g), pyridine (10 ml), dissolved in anhydrous benzenne (2 l), are refluxed under stirring in nitrogen atmosphere for 4 hours. After cooling, the reaction mixture is treated with ethylene glycol (2×200 ml), diluted with ether (1 l), washed with 10% KOH (3×150 ml), washed with water to neutrality, dried on Na$_2$SO$_4$ and evaporated.

After column chromatography (SiO$_2$; h=30 cm, φ=4.3 cm; petroleum ether/ethylether 96/4) 8.5 g of V (m.p. 112°–114° C.) were obtained.

(b) Ethylester of 3α,7β-diacetoxy-22,23-methanate-ursodeoxycholic acid (VI)

A solution of ethyl diazoacetate (EDA) (3.1 ml, 0.03 mol) in cyclohexane (80 ml), has been added, with very slow dripping (2 days), to a suspension of V (8.5 g, 0.02 mol), Cu-Bronze ($\simeq$10 g), in anhydrous cyclohexane (170 ml), refluxed under stirring in nitrogen atmosphere.

The reaction mixture after cooling is filtered and evaporated.

The residue is subjected to column chromatography (SiO$_2$; h=35 cm; φ=3 cm).

By eluting with petroleum ether containing 2% of ethylether, and increasing the percent of ethylether by 1% every 200 ml of eluent until reaching the 7%, there are obtained: a fraction containing V (4.7 g), an α fraction (0.55 g), and α+β fraction (0.9 g), and a β fraction (1.8 g). The NMR spectrum of the α and β fractions is in agreement with the structure VI.

(c) 22,23-Methanate-ursodeoxycholic acid (Ic)

A solution of the β chromatographic fraction (1.8 g) in 15% NaOH in ETOH/H$_2$O (6:4,180 ml) is maintained at reflux under stirring for 4 h. After cooling, the reaction mixture is diluted with H$_2$O, acidified with conc. HCl, and extracted with chloroform. The organic phase is dried on Na$_2$SO$_4$ and evaporated. By column chromatography (SiO$_2$; h=35 cm; φ=2.1 cm) and eluting with chloroform a substance C (240 mg) (m.p. 133°–136° C.) is obtained; going by to elute with chloroform with 2% of methanol a substance D (270 mg) (m.p. 153°–159° C.) in addition to the mixture of the two C+D (370 mg) is obtained. The chemico-physical properties of C and D are in agreement with the structure Ic. Similarly, by hydrolysis of the α fraction two substances A (m.p. 242°–244° C.) and B (m.p. 252°–255° C.) are obtained; the structure Ic can be proposed also for these compounds.

EXAMPLE 2

(a) 3β-Acetoxy-7-keto-Δ$^{22}$-24-norcholene

A mixture of 4α-hydroxy-7-keto-5β-cholan-24-oic acid (nutriacholic acid) (40 g), acetic anhydride (60 ml), and pyridine (58 ml), is left to react overnight, thereafter it is poured on ice and water and extracted with chloroform.

The organic phase is washed with 10% HCl to acidity, then with water to neutrality, dried on MgSO$_4$ and evaporated. The crude reaction product so obtained, without further purification, and moreover Pb(OAc)$_4$ (70 g), Cu(OAc)$_2$ (4 g), pyridine (10 ml), dissolved in anhydrous benzene (2 l), are refluxed under stirring in nitrogen atmosphere for 4 hours. After cooling the reaction mixture is treated with ethyleneglycol (2×200 ml), diluted with ether (1 liter), washed with 10% KOH (3×150 ml), washed with water to neutrality, dried on Na$_2$SO$_4$ and evaporated. Arter column chromatography (SiO$_2$; h=30 cm; φ=3 cm; petroleum ether) 8.5 g of 3α-acetoxy-7-keto-Δ$^{22}$-24-norcholene are obtained.

(b) Ethyl ester of 3α-acetoxy-7-keto-22,23-methanatocholanic acid

A solution of ethyl diazoacetate (EDA) (3.5 ml, 34 mmoles) in cyclohexane (80 ml) is added, with very slot dripping (about 2 days) to a suspension of the compound obtained in (a) (8.5 g; 22 mmoles) and Cu-Bronze ($\simeq$10 g) in anhydrous cyclohexane (200 ml), kept at reflux in nitrogen atmosphere.

After cooling the reaction mixture is filtered and evaporated. The thin layer chromatography shows the formation of products having a lower R$_f$ than the starting substrate, giving evidence of the formation of the desired product.

EXAMPLE 3

(a) 3α,7α-Diacetoxy-24-nor-5β-col-22-ene

A mixture of 3α,7α-diacetoxy-5β-cholanoic acid (16.9 g), lead tetraacetate (33.46 g), copper acetate (1.7 g) and anhydrous pyridine (2 ml) in anhydrous benzene (1 l) is stirred under reflux for 4 hours. The solids are collected on a celite filter. After evaporation of the benzene, the residue is dissolved in ether, washed with 5% aqueous HCl and a 10% sodium bicarbonate solution. The crude extract is chromatographed on silica gel column (750 g). By eluition with ethylacetate-hexane 3:7, the 3,7-diacetoxy-24-nor-5-col-22-ene is obtained (8.3 g, 82%), m.p. 134° C., I.R.: 1730, 1640 cm$^{-1}$. MS: M$^+$=430, m/e=370, 255, 256.

(b) Ethyl 3,7-diacetoxy-22,23-methanate-5-cholanate

A solution of ethyl diazoacetate (3.2 g, 28.1 mmoles) in anhydrous methylene chloride (90 ml) is added dropwise in about 14 h to a suspension of dirhodium (II) tetraacetate (75 mg, 0.17 mmoles) and of the compound obtained in (a), (4 g, 9.3 mmoles) in anhydrous methylene chloride (100 ml) kept under nitrogen atmosphere and under stirring. When the addition is completed, the solvent is evaporated under vacuum and the viscous residue (6.6 g) has been subjected to flash chromatography. By eluting with petroleum ether-ethyl ether 3:2, 1.25 g of the starting product are obtained. By further elution the ethyl 3α,7α-diacetoxy-22,23-methanate-5β-cholanate as a semisolid oil (3.2 g, yield calculated starting from the olefine 67%) is obtained.

IR (nujol) 1720 cm$^{-1}$.

NMR (CDCl$_3$): δ 0.60 (3H, s, C-18 Me), 0.93 (3H, s, C-19 Me), 1.2–1.4 (3H, m, —CO$_2$CH$_2$C$\underline{H}_3$), 2.02 (3H, s, C-7 OCOCH$_3$), 2.03 (3H, s, C-3 OCOC$\underline{H}_3$), 3.9–4.3 (2H, m, —CO$_2$C$\underline{H}_2$CH$_3$), 4.3–4.7 (1H, m, C-3 C$\underline{H}$OAC), 4.7–4.9 1H, m, C-7 C$\underline{H}$OAC).

(c) 3α,7α-Dihydroxy-22,23-methanate-5β-cholanic acid (Id)

A solution of NaOH 9.3N (40 ml) and of the ethyl ester obtained in (b) (3.16 g, 6.1 mmoles) in ethanol (60 ml) is refluxed under stirring. After 4 h the mixture is dropped in iced water (180 ml), extracted with ethyl ether, acidified with 10% hydrochloric acid and extracted with ethylacetate (3×70 ml). The ethyl acetate extracts, collected, are washed with water saturated of sodium chloride and dried on Na$_2$SO$_4$ and the solvent is evaporated under vacuum. There is obtained a solid residue (2.1 g, 85%) m.p. 130°–145° C.

IR (nujol) 3410, 1695 cm$^{-1}$.

NMR (CD$_3$OD) δ 0.65 (3H, s, C-18 Me), 0.93 (3H, s, C-19 Me), 3.1–3.5 (1H, m, C-3 CHOH), 3.6–3.8 (1H, m, C-7 CHOH).

The chemico-physical and pharmacological characteristics of 3α,7β-dihydroxy-5β-cholan-22,23-methanate-24-oic acid (Ic) have been studied in comparison with ursodeoxycholic acid.

CHEMICO-PHYSICAL PROPERTIES

Compound (Ic) showed values of solubility in water at 37° C. (16 μM) and of pK$_a$ (4.7) very similar to those of ursodeoxycholic acid. The critic micellar concentration (CMC), determined by the method of azulene dissolution, proved to be on the contrary lower for Ic (5 mM) in comparison with the reference compound (8 mM), perhaps because of the lower hydrophobicity of the latter.

PHARMACOLOGICAL PROPERTIES

The metabolism of (Ic) in the rat has been studied in comparison to that of ursodeoxycholic acid, after endovenous administration of 50 mg/animal of both compounds, both as bolus and as slow infusion (1 mg/min.). The bile was collected every 15 min. for three hours. The compound (Ic) in a single passage through the liver, is conjugated with taurine only for 70% while the 30% is excreted as a free acid; the reference compound is on the contrary excreted for 95–97% as conjugated. Moreover (Ic) exhibits a clearly higher choleretic effect, along with a longer duration of action and an increase of the hourly secretion of the three biliary lipids, in a particularly selective way for phospholipids and biliary acids.

Therefore, due to their remarkable choleretic effect and the positive effect on the biliary secretion, above all in comparison with physiological derivatives, the compounds of the invention are useful as choleretics, eupeptics, antidyspeptics, antidyslipidemics, in the treatment of calcuclosis and generally in the treatment of all pathologic conditions wherein a stimulus of the bile flow and a qualitative and quantitative modification of the biliary composition are necessary. An essential aspect of the present invention is therefore provided by pharmaceutical compositions containing as active principle at least one of the compounds of formula I, in addition to the excipients of convential use in pharmaceutical technique. The compounds of the invention can be administered at doses ranging from 10 and 250 mg 2–3 times a day by the oral route, for instance in form of capsules, tablets, sugar-coated pills, monodose sachets or by local perfusion before of surgical operations in form of solution of dispersable powders.

We claim:

1. A bilary acid compound of formula I

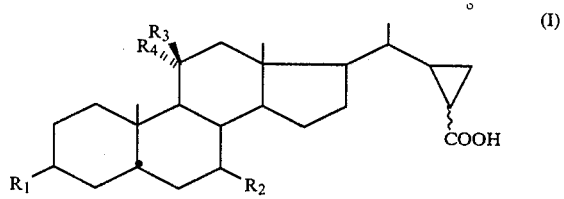

wherein R$_1$ and R$_2$ are an hydroxy group being α or β oriented; R$_3$ is hydrogen and R$_4$ is an hydroxy group or vice versa, or R$_3$ and R$_4$, taken together, form a keto group, and pharmaceutically acceptable salts thereof with alkaline or alkali-earth metals, or with organic bases and stereoisomers thereof.

2. A compound according to claim 1, which is 3α,7α,12α-trihydroxy-5β-cholan-22,23-methanate-24-oic acid (22,23-methanate-cholic acid), (Ia).

3. A compound according to claim 1, which is 3α,7β,12α-trihydroxy-5β-cholan-22,23-methanate-24-oic acid (Ib).

4. A compound according to claim 1, which is 3α,7β-dihydroxy-5β-cholan-22,23-methanate-24-oic acid (22,23-methanate-ursodeoxycholic acid) (Ic).

5. A compound according to claim 1, which is 3α,7α-dihydroxy-5β-cholan-22,23-methanate-24-oic acid (22,23-methanate-chenodeoxycholic acid) (Id).

6. A compound according to claim 1, which is 3α-hydroxy-7-keto-5β-cholan-22,23-methanate-24-oic acid (3α-hydroxy-7-keto-22,23-methanate-cholanic acid) (Ie).

7. A process for the preparation of a compound according to claim 1, wherein an ester of formula (II)

wherein St' represents the etiocholanyl residue having two or more acyloxy groups both in the α or β conformation, some of which being optionally replaced by keto groups, and R is a C$_1$–C$_4$ alkyl residue, is subjected to hydrolysis of the ester group in an hydroalcoholic solution of an alkali metal hydroxide.

8. Pharmaceutical composition characterized by containing as active principle the compound according to claim 2.

9. Pharmaceutical composition characterized by containing as active principle the compound according to claim 3.

10. Pharmaceutical composition characterized by containing as active principle the compound according to claim 4.

11. Pharmaceutical composition characterized by containing as active principle the compound according to claim 5.

12. Pharmaceutical composition characterized by containing as active principle the compound according to claim 6.

13. A pharmaceutical composition containing as an active ingredient an effective amount of at least one compound of formula I

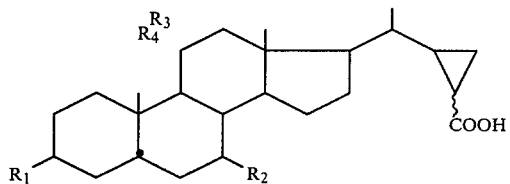

wherein $R_1$ and $R_2$ are an hydroxy group being α or β oriented; $R_3$ is hydrogen and $R_4$ is an hydroxy group or vice versa, or $R_3$ and $R_4$, taken together, form a keto group, and pharmaceutically acceptable salts thereof with alkaline or alkali-earth metals, or with organic bases and stereoisomers thereof, together with a pharmaceutically acceptable carrier or diluent.

14. A pharmaceutical composition as in claim 13, wherein said active ingredient is a member selected from the group consisting of 3α,7α,12α-trihydroxy-5β-cholan-22,23-methanate-24-oic acid (22,23-methanate-cholic acid), 3α,7β,12α-trihydroxy-5β-cholan-22,23-methanate-24-oic acid, 3α,7β-dihydroxy-5β-cholan-22,23-methanate-24-oic acid (22,23-methanate-ursodeoxycholic acid), 3α,7α-dihydroxy-5β-cholan-22,23-methanate-24-oic acid (22,23-methanate-chenodeoxycholic acid), 3α-hydroxy-7-keto-5β-cholan-22,23-methanate-24-oic acid (3α-hydroxy-7-keto-22,23-methanate-cholanic acid).

* * * * *